US008019406B2

United States Patent
Lian et al.

(10) Patent No.: US 8,019,406 B2
(45) Date of Patent: Sep. 13, 2011

(54) APPARATUS AND METHOD TO ASSESS THE RISK OF R-ON-T EVENT

(75) Inventors: Jie Lian, Beaverton, OR (US); Dirk Muessig, West Linn, OR (US); Volker Lang, West Linn, OR (US)

(73) Assignee: Biotronik CRM Patent AG, Baar (CH)

( * ) Notice: Subject to any disclaimer, the term of this patent is extended or adjusted under 35 U.S.C. 154(b) by 757 days.

(21) Appl. No.: 12/045,142

(22) Filed: Mar. 10, 2008

(65) Prior Publication Data

US 2009/0228061 A1  Sep. 10, 2009

(51) Int. Cl.
*A61N 1/362* (2006.01)
*A61B 5/0452* (2006.01)
(52) U.S. Cl. .......................... 600/509; 607/9
(58) Field of Classification Search .............. 600/509, 600/508; 607/14, 25, 9
See application file for complete search history.

(56) References Cited

U.S. PATENT DOCUMENTS

| 6,512,951 | B1 | 1/2003 | Marcovecchio et al. | |
|---|---|---|---|---|
| 2003/0101080 | A1* | 5/2003 | Zizzamia et al. | 705/4 |
| 2004/0220631 | A1* | 11/2004 | Burnes et al. | 607/9 |
| 2007/0010578 | A1* | 1/2007 | Chien et al. | 514/483 |

FOREIGN PATENT DOCUMENTS

EP  1 923 097  5/2008

OTHER PUBLICATIONS

European Search Report, dated Jun. 17, 2009.

* cited by examiner

*Primary Examiner* — Carl H Layno
*Assistant Examiner* — Pamela M Bays
(74) *Attorney, Agent, or Firm* — Arc IP Law, PC; Joseph J. Mayo (57) ABSTRACT

A medical device and a method is suggested for assessing the risk of R on T events. The device comprises a memory, input means for acquiring or receiving an electrogram signal and processing means. The processing means are adapted to detect R-wave and T-waves represented by said electrogram, establish a QT-RR regression model based detected R-waves and T-waves, estimate a vulnerable period, and store estimated vulnerable period data in said memory. Likewise, the method comprises the steps of to detecting R-wave and T-waves represented by an electrogram, establishing a QT-RR regression model based detected R-waves and T-waves, estimating a vulnerable period, and storing estimated vulnerable period data.

16 Claims, 10 Drawing Sheets

APPARATUS AND METHOD TO ASSESS THE RISK OF R-ON-T EVENT

BACKGROUND OF THE INVENTION

1. Field of the Invention

The present invention generally relates to medical devices and systems that incorporate an apparatus and method to assess the risk of R-on-T event, based on analysis of the surface ECG or the intracardiac electrogram (IEGM). The risk assessment of R-on-T event can be further used for risk stratification of ventricular tachyarrhythmias, prediction and prevention of ventricular tachycardiac (VT) and/or ventricular fibrillation (VF), and facilitating fast and robust detection of VT/VF onset.

The present invention particularly relates to implantable heart stimulators, including pacemakers, defibrillators and cardiovertors, which stimulate cardiac tissue electrically to control the patient's heart rhythm. The present invention also relates to external cardiac monitors, portable Holter monitors, and automatic external defibrillators (AEDs) that are capable to measure, record, and analyze the surface ECG.

2. Description of the Related Art

A R-on-T event is a premature ventricular event (R-wave) interrupting the T wave of the preceding beat. A R-on-T event often predisposes to serious ventricular arrhythmias.

With respect to artificial heart stimulators such as implantable cardiac pacemakers determination of the duration of an individual's R-T interval is important in order to prevent stimulation of the ventricle during this interval because the ventricular myocardium is not fully repolarized then. During the ventricular repolarization the ventricle is susceptible to fibrillation. Therefore, the time interval prior to the T-wave is called vulnerable period (VP). The T-wave precedes the end of the vulnerable phase.

The QT-RR relationship has been extensively investigated during the past decades. It is well known that the QT interval is rate-dependent. In order to compare the QT interval recorded at different heart rates, effort has been made to estimate the heart-rate corrected QT interval (QTc), which relates the QT interval with the RR interval in a predefined mathematical formula, based on statistical regression analysis. Although dozens of QTc formulas have been proposed (linear model, hyperbolic model, parabolic model, etc.), controversial results on optimal regression parameters have been reported.

BRIEF SUMMARY OF THE INVENTION

It is an object of the invention to provide means for reliable assessment of an individual's Q-T interval duration.

It is a further object of a preferred embodiment of the invention to provide means for assessment of the risk of R-on-T event for an individual.

According to the present invention, the risk of R-on-T event for each beat is assessed quantitatively in real time by comparing the timing of the R wave with the vulnerable period (VP) estimated from the preceding RR intervals. As described below in details, three steps are involved:

(1) establish a QT-RR regression model;
(2) estimate a vulnerable period (VP); and, preferably,
(3) calculate a risk score of R-on-T event.

The invention is based on the insight that recent studies have suggested that the QT-RR relationship could be individually optimized. It was demonstrated that the QT-RR relationship has remarkable intra-subject stability. These studies clearly showed that, on one hand, there is no optimal QTc formula (neither regression parameters nor the curvature of the model itself) that is applicable to all subjects. On the other hand, it is feasible to estimate relatively accurate QT interval from the RR intervals, provided that the subject-specific QT-RR relationship is properly established a priori.

BRIEF DESCRIPTION OF THE DRAWINGS

The above and other aspects, features and advantages of the present invention will be more apparent from the following more particular description thereof, presented in conjunction with the following drawings wherein.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

Implantable Heart Stimulator

Figure 1:
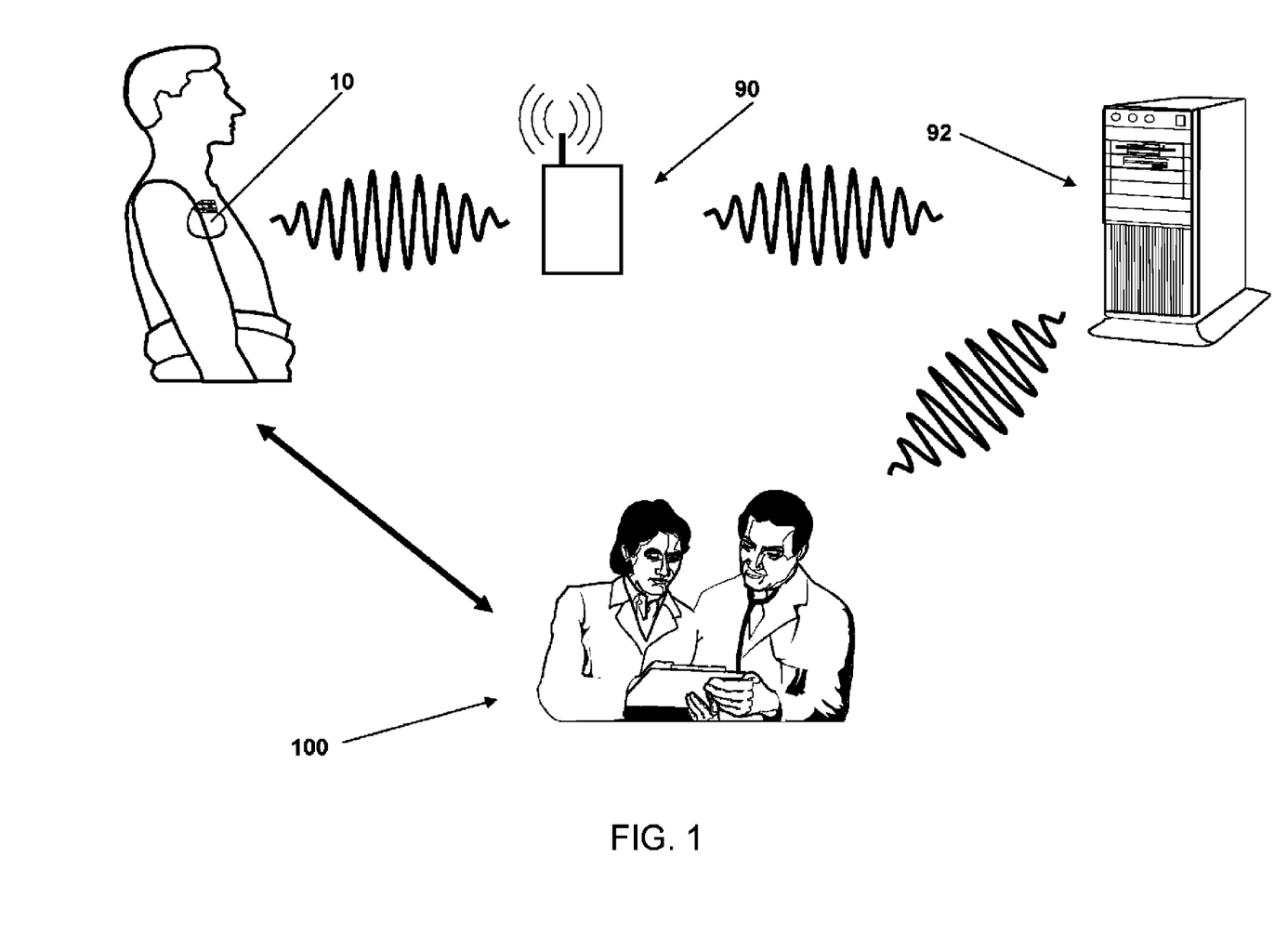
FIG. 1 is an overview over a cardiac therapy system including an implantable heart stimulator, an external device and a central service center.

The therapy system depicted in FIG. 1 comprises an implantable medical device 10 which is a three chamber pacemaker (heart stimulator) implanted into a patient (subject) 12. The therapy system further comprises an external device 90 and a service center 92. The implantable medical device 10 and the external device 90 allow for a short-range wireless data communication for data exchange between implantable medical device 10 and the external device 90. External device 90 serves as a relay station between the implantable medical device and a central service center 92. Thus, data may be exchanged between the implantable device 10 and the central service center 92. A physician attending a patient thus can access all data provided by the implantable medical device 10 via the central service center 92. Further, any data processing requiring a considerable amount of computing power can be carried out by the external device 90 or in the service center 92. This particularly applies to that kind of data processing that only needs to be carried out from time to time in contrast to that kind of data processing that is to be carried online (that is, at least approximately in real time). The later data processing includes evaluation of intracardic electrograms for the detection of e.g. fibrillation that needs to be treated.

As will be more apparent from the following description of the implantable medical device 10, the implantable medical device 10 is capable of making up intracardiac electrograms that represent an electrical activity of the myocardium of either a right atrium or a right ventricle of a heart. According to further embodiments not represented in detail within this disclosure the implantable medical device could also be capable of picking up intracardiac electrograms for the left atrium and/or the left ventricle. Further, the implantable medical device is capable of creating a far field electrogram signal from intracardiac electrogram signals picked up via intracardiac electrodes connected to the implantable medical device 10.

Figure 2:
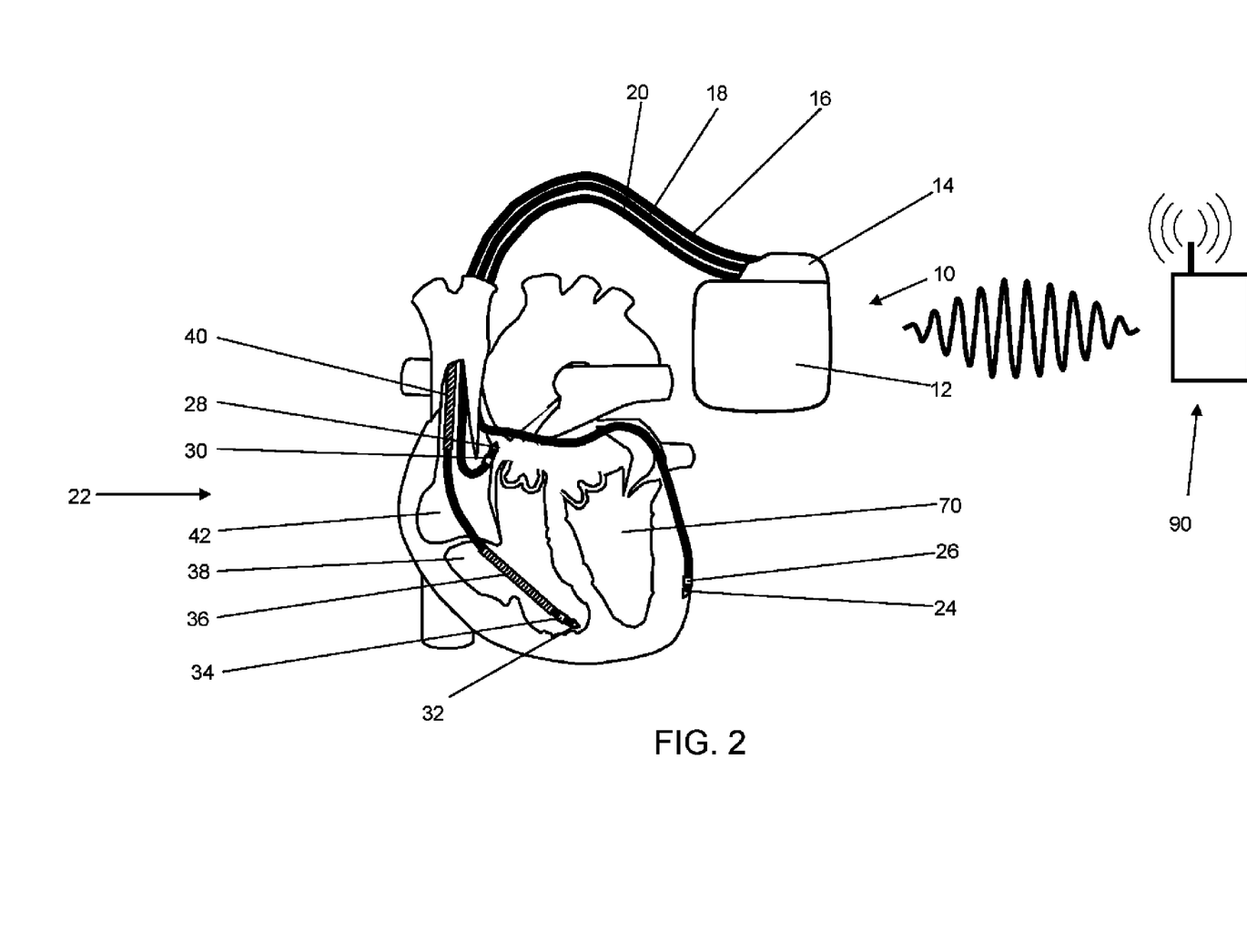
FIG. 2 illustrates the heart stimulator connected to electrode leads that are placed in a heart together with an external device.

From FIG. 2 it is apparent that the heart stimulator 10 comprises a case 12 and header 14.

The heart stimulator 10 is connected to three electrode leads, namely a right ventricular electrode lead for 16, a right atrial electrode lead 18 and a left ventricular electrode lead 20.

The left ventricular electrode lead 20 is designed to pass trough the coronary sinus of heart 22. A typical electrode lead suitable for use with heart stimulator 10 is the electrode lead Corox+UP/BB by the applicant. Left ventricular electrode lead 20 comprises a left ventricular tip electrode 24 at the distal end of left ventricular electrode lead 20 and a left ventricular ring electrode 26.

Atrial electrode lead 18 comprises a right atrial tip electrode 28 at the distal end of right atrial electrode lead 18 and a right atrial ring electrode 30.

The right ventricular electrode lead 16 comprises right ventricular tip electrode 32 at the distal end of right ventricular electrode lead 16 and a right ventricular ring electrode 34.

In order to illustrate that heart stimulator 10 may be adapted to act as an implantable cardioverter/defibrillator (ICD), ventricular electrode lead 16 also exhibits a ventricular shock coil 36 for the delivery of defibrillation shocks to right ventricle 38 of heart 22 and a superior vena cava (SVC) shock coil 40 for the delivery of defibrillation shocks to a right atrium 42 of heart 22.

Each electrode and shock coil of electrode leads 16 to 20 is separately connected to an electric circuit enclosed by case 12 of heart stimulator 10 by way of electrical contacts of a plug (not shown) at the proximal end of each electrode lead 16 to 20 and corresponding contacts (not shown) in header 14 of heart stimulator 10.

Figure 3:
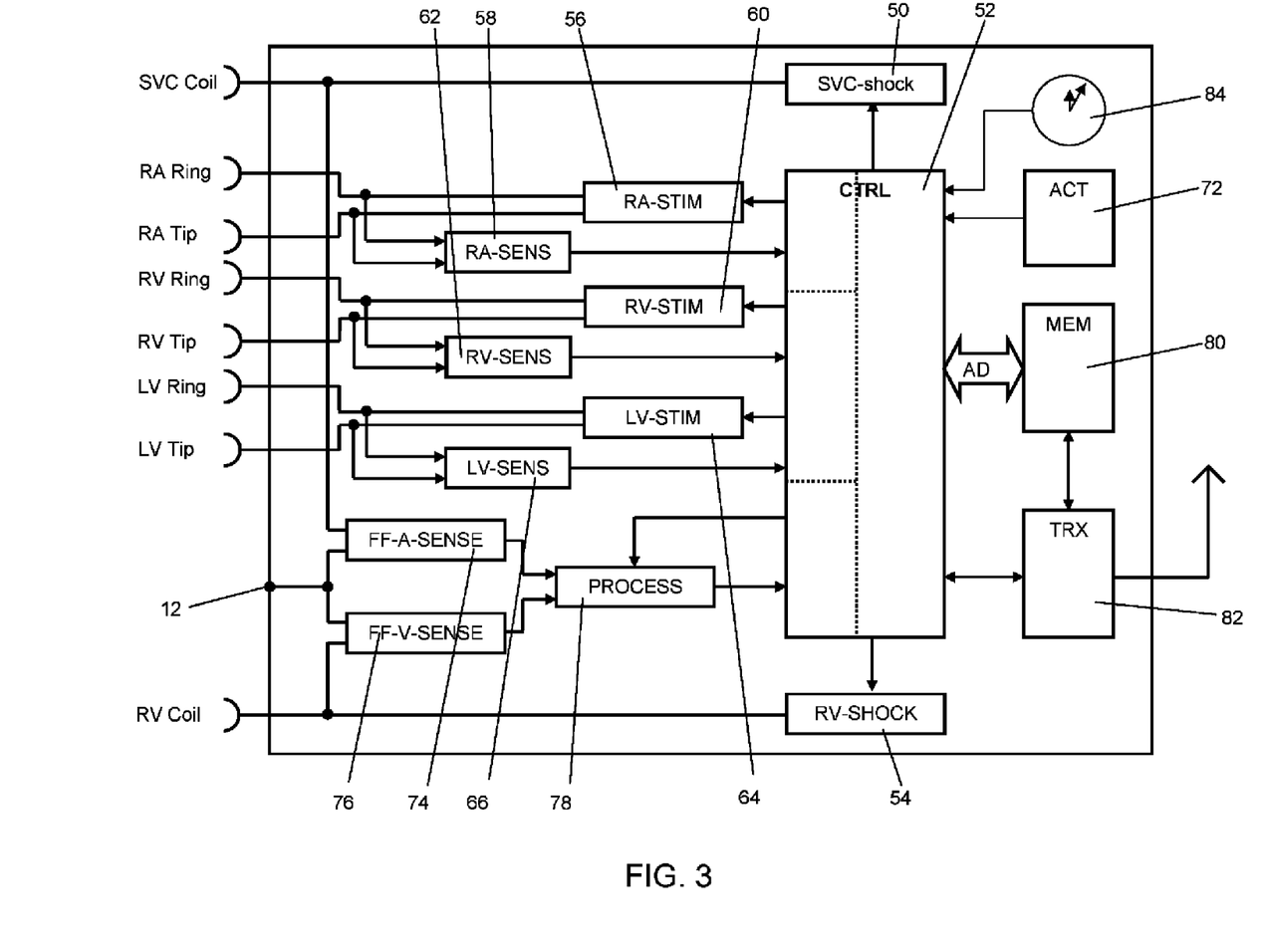
FIG. 3 shows a schematic block diagram of the heart stimulator of FIG. 1.

Now refer to FIG. 3. SVC shock coil 40 is connected to right atrial shock generator 50 that is controlled by a control unit 52 of heart stimulator 10.

Similarly, right ventricular shock coil 36 is connected to a right ventricular shock generator 54 that is also connected to control unit 52.

Right atrial tip electrode 28 and right atrial ring electrode 30 are both connected to a right atrial stimulation pulse generator 56 and a right atrial sensing stage 58 that are internally both connected to control unit 52.

Right atrial stimulation pulse generator 56 is adapted to generate atrial stimulation pulses of sufficient strength to cause an excitation of atrial myocardium by an electrical pulse delivered via right atrial tip electrode 28 and right atrial ring electrode 30. Preferably, means are provided to adapt the right atrial stimulation pulse strength to the stimulation threshold in the right atrium.

Right atrial sensing stage 58 is adapted to pick up myocardial potentials indicating an intrinsic atrial excitation that corresponds to a natural atrial contraction. By way of right atrial sensing stage 58, it is possible to stimulate the right atrium 42 of heart 22 in a demand mode wherein a right atrial stimulation pulse is inhibited if an intrinsic atrial event (intrinsic atrial excitation) is sensed by right atrial sensing stage 58 prior to expiration of an atrial escape interval.

In a similar manner, right ventricular ring electrode 34 and right ventricular tip electrode 32 are connected to right ventricular stimulation pulse generator 60 and to a right ventricular sensing stage 62 that in turn are connected to control unit 52. By way of right ventricular tip electrode 32, right ventricular ring electrode 34, right ventricular stimulation generator 60 and right ventricular sensing stage 62, right ventricular stimulation pulses can be delivered in a demand mode to the right ventricle 38 of heart 22.

Right ventricular sensing stage 62 is adapted to pick up myocardial potentials indicating an intrinsic right ventricular excitation that corresponds to a natural right ventricular contraction. By way of right ventricular sensing stage 62, it is possible to stimulate the right ventricle 38 of heart 22 in a demand mode wherein a right ventricular stimulation pulse is inhibited if an intrinsic right ventricular event (intrinsic right ventricular excitation) is sensed by right ventricular sensing stage 62 prior to expiration of a right ventricular escape interval.

In the same way left ventricular tip electrode 24 and left ventricular ring electrode 26 are connected to the left ventricular stimulation pulse generator 64 and the left ventricular sensing stage 66 that are internally connected to control unit 52 and that allow for stimulating a left ventricle 70 of heart 22.

Left ventricular sensing stage 66 is adapted to pick up myocardial potentials indicating an intrinsic left ventricular excitation that corresponds to a natural left ventricular contraction. By way of left ventricular sensing stage 66, it is possible to stimulate the left ventricle 70 of heart 22 in a demand mode wherein a left ventricular stimulation pulse is inhibited if an intrinsic left ventricular event (intrinsic left ventricular excitation) is sensed by left ventricular sensing stage 66 prior to expiration of a left ventricular escape interval.

Triggering and inhibition of delivery of stimulation pulses to the right atrium, the right ventricle or the left ventricle is controlled by control unit 52, in a manner known to one skilled in the art. The timing that schedules delivery of stimulation pulses if needed is con-trolled by a number of intervals that at least partly may depend on a hemodynamic demand of a patient that is sensed by means of an activity sensor 72 that is connected to control unit 52. Activity sensor 72 allows for rate adaptive pacing wherein a pacing rate depends on a physiological demand of a patient that is sensed by a way of activity sensor 72.

For the purpose of composition of a far-field intra-atrial electrogram (AEGM) and a far-field intra-ventricular electrogram (VEGM) a far-field atrial sensing stage 74 and a far-field ventricular sensing stage 76, respectively, are provided. The far-field atrial sensing stage 74 is connected to a case electrode that is formed by at least an electrically conducting part of case 12 of the heart stimulator 10 and to the SVC coil electrode 40 or the right atrial ring electrode 30.

The far-field ventricular sensing stage 76 is also connected to the case electrode formed by a case 12 of heart stimulator 10 and to the right ventricular coil electrode 36 or the right ventricular ring electrode 34 or the left ventricular ring electrode 26. Both, far-field atrial sensing stage 74 and far-field ventricular sensing stage 76, are adapted to pick up far-field intra-cardiac electrograms and to generate electrogram signals that are fed to a processing unit 78. Processing unit 78 is adapted to filter and scale each electrogram signal received from either the far-field atrial sensing stage 74 or the far-field ventricular sensing stage 76 or both independently from each other and to sum the resulting filtered and scaled electrogram signals in order to generate the composite far-field electrogram signal.

Thus the heart stimulator can provide different kinds of electrograms such as far-field electrograms similar to surface electrocardiograms (surface ECG) and intracardiac electrograms (IEGM) for further evaluation and QT interval analysis in particular. According to alternative embodiments of the invention, the evaluation is either carried out by the control unit 40 of heart stimulator 10 or be external device 90 or at the service center 92.

QT-RR Regression Model

In a preferred embodiment, the patient is monitored during a calibration period when the RR intervals and QT intervals are measured from surface ECG or IEGM. Then statistical regression analysis of the QT-RR relationship is conducted to obtain the patient-specific QT-RR regression model. Different regression models (linear model, hyperbolic model, parabolic model, etc.) with different regression parameters are tested to search for the optimal QT-RR regression model, which is defined to have the lowest residuum between modelled data and measured data.

Specifically for implantable heart stimulators, such statistical regression analysis can be conducted offline in the external device, and the resulting optimal QT-RR regression model and its parameters are programmed into the implantable device. To facilitate firmware implementation and reduce computation cost, a QT-RR lookup table can be pre-calculated based on the regression model and downloaded into the implant device memory 80. Preferably, the calibration and regression analysis of QT-RR relationship is taken for each subject prior to device implantation, during each follow-up, and every time after change of drug therapy.

In a preferred embodiment, the QT-RR regression analysis is performed based on standard surface ECG obtained during 24-hour Holter recording, or can be obtained with minutes of ECG recording during a treadmill test with predefined exercise protocol that covers certain heart rate range. In another embodiment, if QT-RR calibration data is not available, a generic regression model with predefined model parameters is used. One exemplary model is the parabolic model $QT=\beta \cdot RR^{\alpha}$, where $\alpha=\frac{1}{3}$, $\beta=0.45$. However, optimization of the regression model should be performed whenever the updated QT-RR data are available.

Although the QT interval is mainly dependant on heart rate, the effects of other factors such as the autonomic tone and the "lag hysteresis" may also affect the QT interval. According to the present invention, one means to include the "lag hysteresis" effect is by estimating QT interval from the weighted average of multiple preceding RR intervals. Such a moving weighted average method can approximately simulate the delayed QT-RR response to sudden heart rate change, thus partially compensate for the "lag hysteresis". It is likely that the QT-RR relationship may exhibit certain circadian pattern, considering varying levels of autonomic modulation, thus corresponding adjustment of regression parameters for day and night may be implemented.

Estimation of VP

Figure 4:
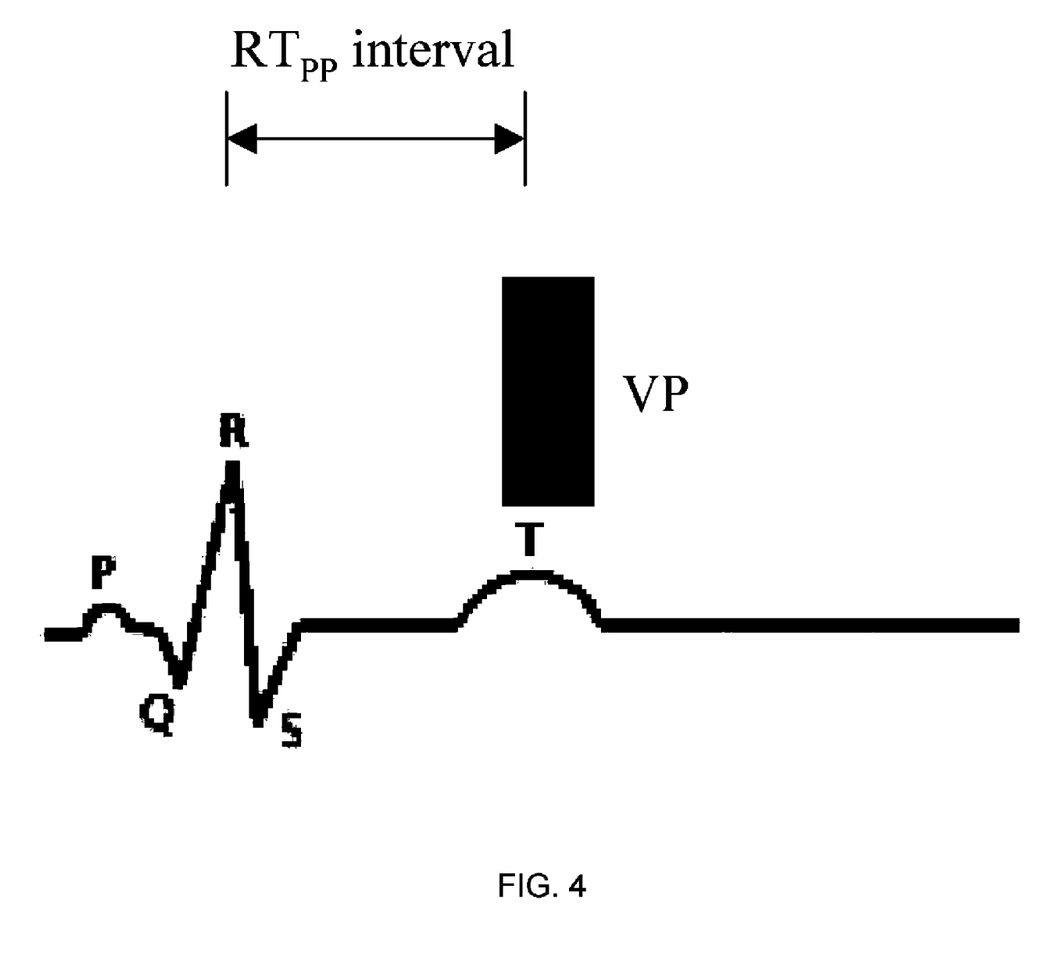
FIG. 4 is an illustration of the vulnerable period and the $RT_{PP}$ interval.

Conventional QT interval is defined as the interval from the beginning of Q wave to the end of T wave, which is difficult to measure because there is inherent imprecision in identifying the end of the T wave from the surface ECG. For the purpose of estimating VP, such problems may be avoided. Because VP usually refers to the portion of the T wave near the peak and early downslope (FIG. 4), it is sufficient to determine the peak of T wave, then set VP around the peak of T wave. For example, denote $RT_{pp}$ as the interval from the peak of R wave to the peak of T wave, the VP (from t1 to t2 with respect to the peak of R wave) can be estimated as: $VP=(t1, t2)=(RT_{PP}-20 ms, RT_{PP}+20 ms)$, i.e., from 20 ms before to 20 ms after the peak of T wave. Alternatively, the lower and upper boundaries of VP (t1, t2) may also be estimated using the same QT-RR regression formula. For example, if the QT-RR regression model is $QT=\beta \cdot RR^{\alpha}$, then the lower and upper boundaries of VP (t1, t2) may be estimated by $t1=(\beta-\delta 1) \cdot RR^{\alpha}$ and $t2=(\beta+\beta 2) \cdot RR^{\alpha}$, respectively, where $\delta_1$ and $\delta_2$ are small positive constants. Therefore, it is not necessary to identify the T wave offset for QT interval measurement. Instead, the task becomes much easier to measure the $RT_{PP}$ interval, i.e., the time interval between peak of R wave and peak of T wave (FIG. 4). Based on the measured RR interval and $RT_{PP}$ interval data, similar regression analysis can be performed to determine the $RT_{PP}$-RR relationship. Once such a regression model is determined, the boundaries of VP can be estimated given a preset window width, see FIG. 4: Illustration of the vulnerable period and the $RT_{PP}$ interval.

Figure 10:
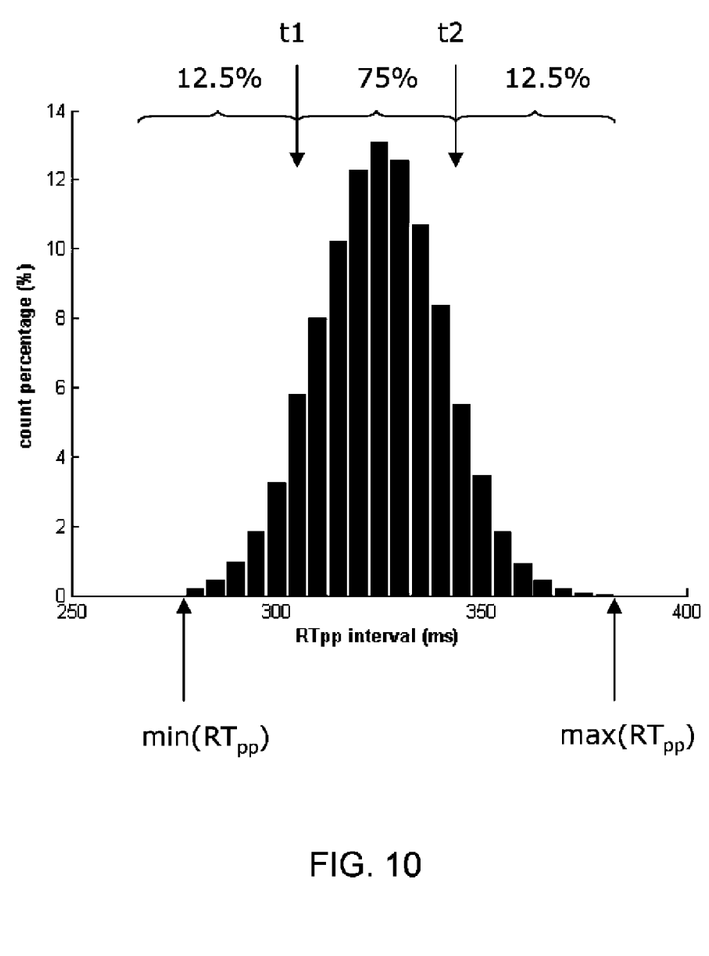
FIG. 10 shows by way of an example of $RT_{pp}$ distribution for a given RR interval (or a binned RR interval range) how the upper and lower boundaries of the VP for this RR interval (or binned RR interval range) can be determined based on this $RT_{pp}$ distribution.

Yet in another embodiment, the estimation of the VP boundaries can be directly estimated from the $RT_{PP}$-RR plot, that is, without the computation effort of the regression analysis. More specifically, a 2D scatter graph is obtained by plotting all pairs of $(RT_{PP}, RR)$ values. For each RR interval (or a binned RR interval range), there is a distribution of the corresponding $RT_{PP}$ intervals (FIG. 10), which could be used to define the boundaries of the VP for this RR interval (or the binned RR interval range). By examining the distribution of $RT_{PP}$ intervals corresponding to each RR interval (or binned RR interval range), a complete VP zone can be defined. As illustrated in FIG. 10, in one example, the upper and lower boundaries of the VP for this RR interval (or the binned RR interval range) could be respectively defined as the maximum and minimum of the corresponding $RT_{PP}$ intervals. In another example, the upper boundary (t2) and the lower boundary (t1) of the VP for this RR interval (or the binned RR interval range) could be determined such that a programmable percentile (e.g., 75%) of the $RT_{PP}$ intervals are bounded between t1 and t2, while the outliers (i.e., $RT_{PP}<t1$ and $RT_{PP}>t2$) are symmetrically distributed.

In the following, the terms QT interval and $RT_{PP}$ interval are used inter-changeably for simplicity purpose, with the understanding that the VP boundaries can be estimated based on either QT-RR interval analysis, or $RT_{Pp}$-RR interval analysis.

Risk Score of R-on-T Event

Figure 5:
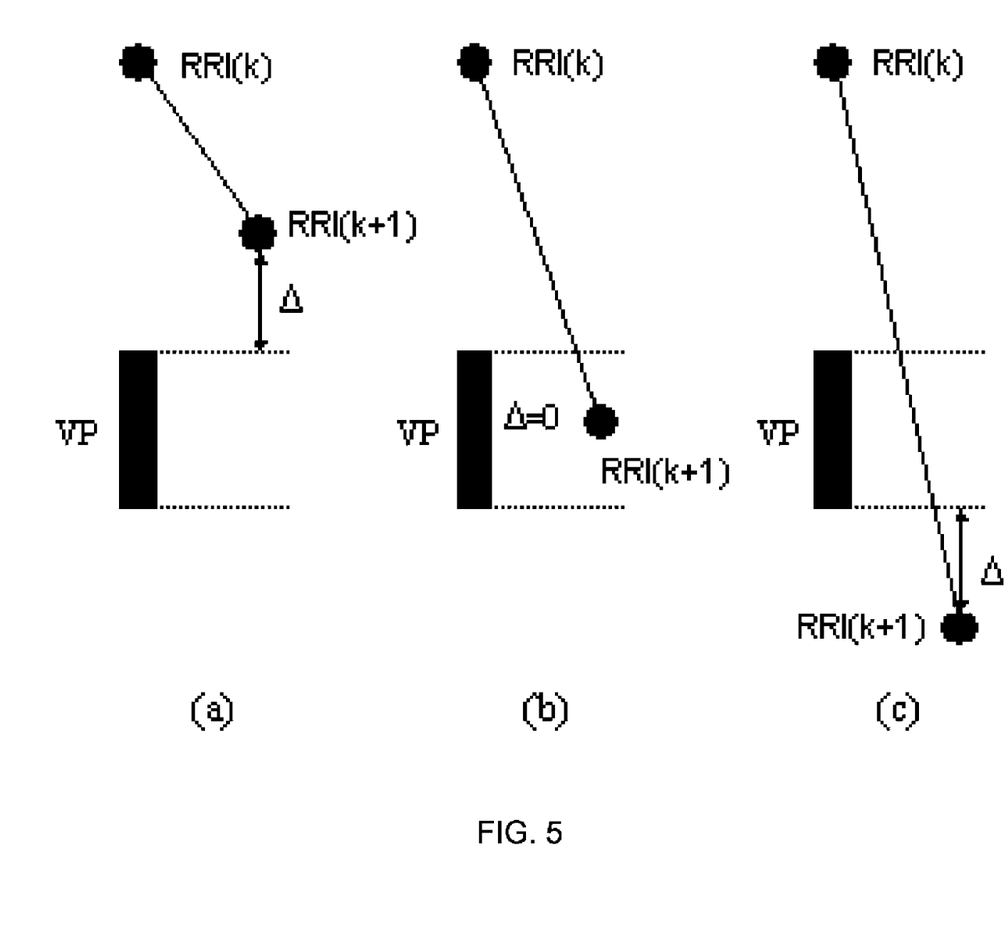
FIG. 5 is an illustration of the possible relationship between estimated VP and the subsequent RR interval.

According to a preferred embodiment of the present invention, the incidence of R-on-T event is considered as a stochastic process. In other words, given an estimated VP and the subsequent RR interval, the risk of R wave (paced or sensed) overlapping with VP is evaluated as a random variable. FIG. 5 illustrates the concept in more details: The VP boundaries can be estimated from the RR interval for the k-th beat, RRI(k). The following beat occurs with RR interval RRI(k+1), which can be (a) longer than the upper boundary of the VP, (b) fall into the VP, or (c) shorter than the lower boundary of the VP. If the boundaries of VP are precisely accurate, then the probability of R-on-T event is 0 for the cases (a) and (c), and is 1 for the case (b). However, because the VP is estimated and its accuracy may be affected by many factors, there is possibility that R-on-T events occur in the cases (a) and (c), or R-on-T events not occur in the case (b). See FIG. 5: Illustration of the possible relationship between estimated VP and the subsequent RR interval.

There are many methods to quantify such a probabilistic problem. According to an exemplary embodiment, the following index, risk score (RS), is calculated to quantify the probability of R-on-T event:

$$RS = Ae^{-\Delta^2/\sigma^2}$$

Figure 6:
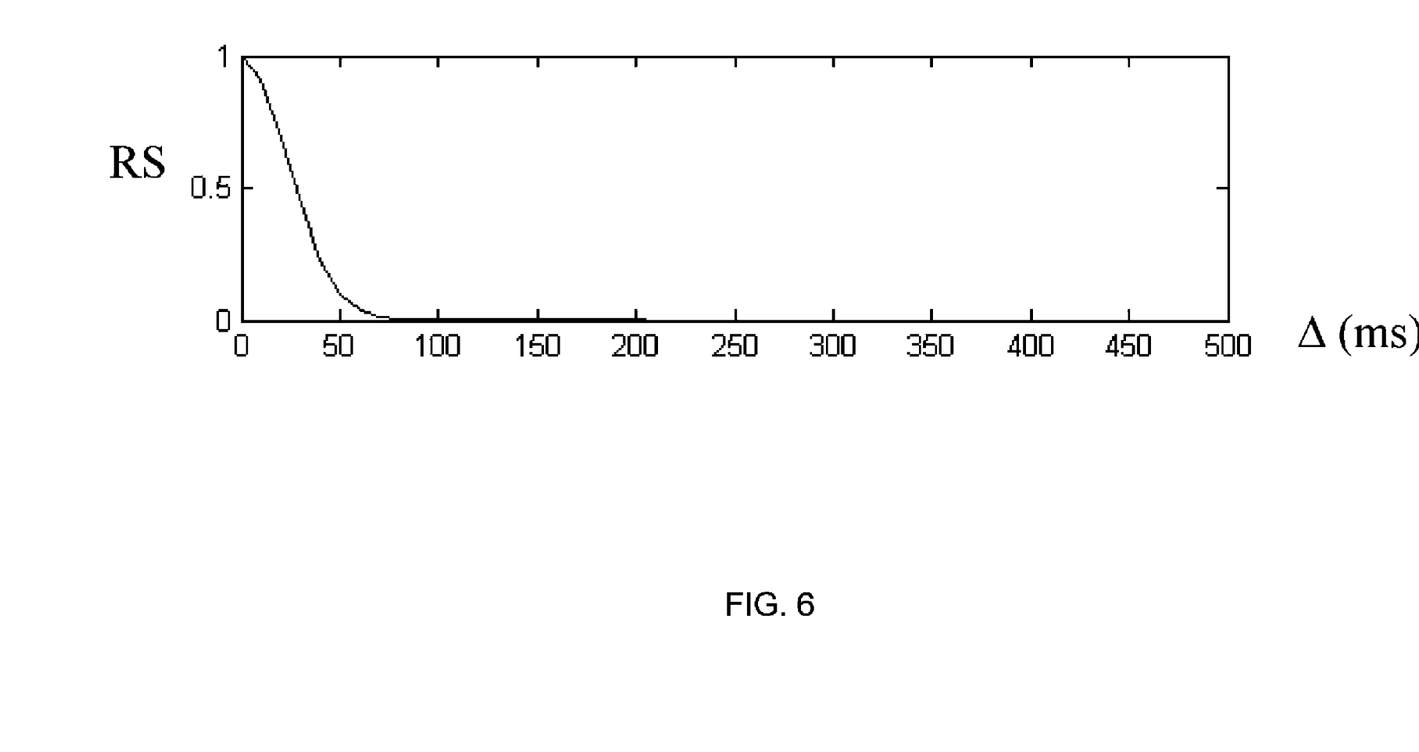
FIG. 6 is an illustration of the function curvature for the proposed risk score metric.

Here, $\Delta$ is the absolute time difference (unit: ms) between $RRI(k+1)$ and the nearest VP boundary for the cases (a) and (c), and is 0 for the case (b). The parameter A is a constant, defining the probability of R-on-T event in the case of $\Delta=0$. The parameter $\sigma$ controls the sensitivity of RS with respect to the change of $\Delta$, by adjusting the width of the function curve, as illustrated in FIG. 6. In this example, $A=1.0$, $\sigma^2=-50^2/\ln(0.1)$, thus it implies $RS=1.0$ for $\Delta=0$, and $RS=0.1$ for $\Delta=50$ ms. Clearly, by comparing the estimated VP and the subsequent RR interval, the beat with smaller $\Delta$ has higher risk to develop R-on-T event (probability approaches to 1.0 when $\Delta$ is close to 0), whereas the beat with larger $\Delta$ has lower risk to develop R-on-T event (probability approaches to 0.0 when $\Delta$ is large enough).

As discussed above, by performing the regression analysis, the optimal $RT_{PP}$-RR model can be determined by minimizing the residuum between modeled and measured RR intervals. In addition, the $RT_{PP}$ variance (correspondingly the possible range of VP boundaries) for each RR interval can be obtained from the same regression analysis. Therefore, it is reasonable to adjust the width of the RS curve (controlled by $\sigma$) based on the results of regression analysis, to achieve desired estimation confidence. For example, if the regression analysis shows that more than p (in percentage) measured $RT_{PP}$ are within $\pm d$ (in ms) range of the model-predicted $RT_{Pp}$, then the RS can be considered as 1-p when $\Delta=d$, by setting $\sigma^2=-d^2/\ln((1-p)/A)$. Note that such an adjustment of RS can be performed for each different RR interval based on its own $RT_{PP}$ variance (i.e., $\sigma$ is a function of heart rate), or can be done once based on the average $RT_{PP}$ variance over all RR intervals. See FIG. 6: Illustration of the function curvature for the proposed risk score metric.

Early Detection of VT/VF

According to a particular preferred embodiment, the estimation of R-on-T event is used for early detection of VT/VF.

Figure 7:
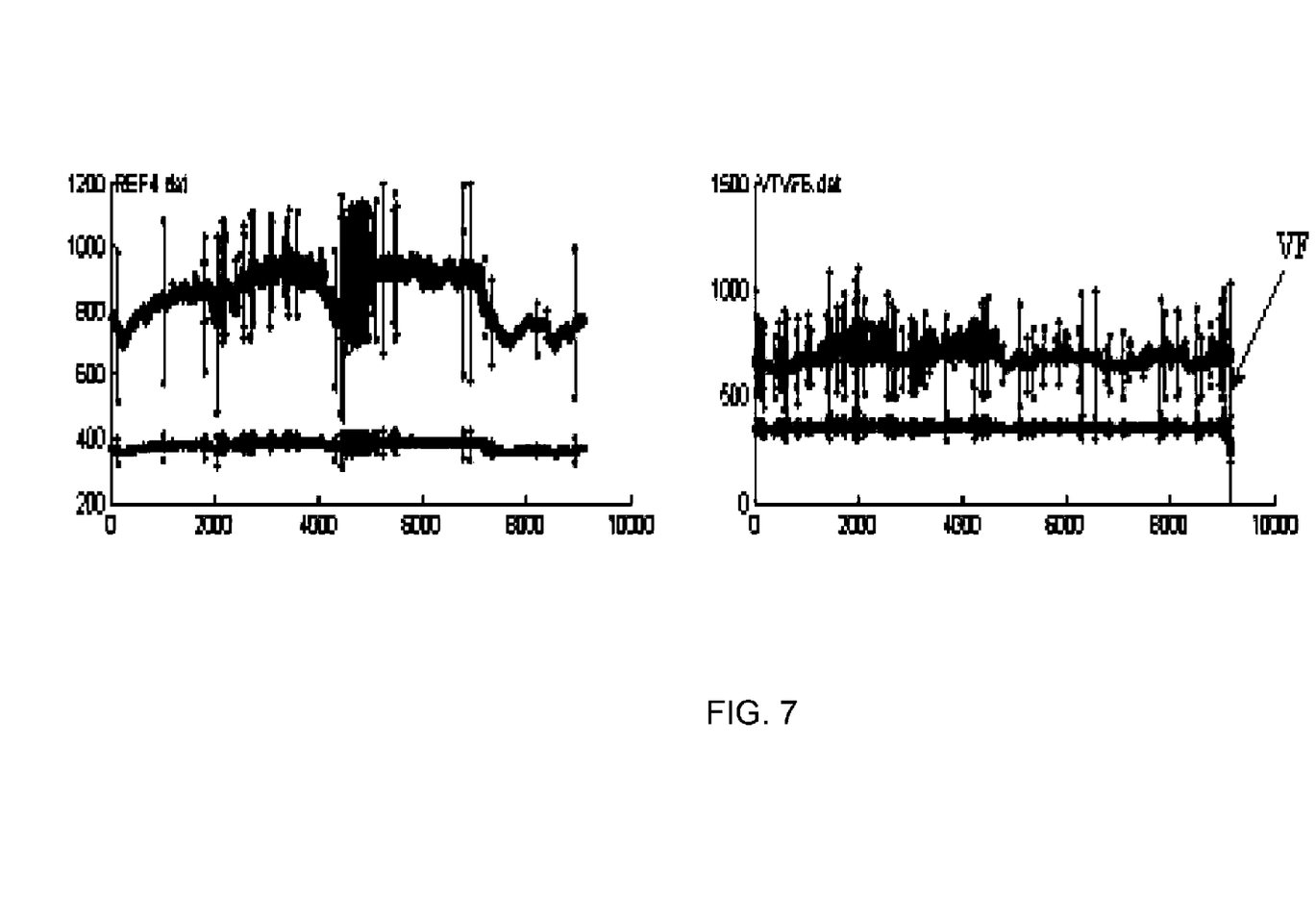
FIG. 7 shows the prediction of a R-on-T event at onset of VF but no event for reference recording.

FIG. 7 shows one example, in which a generic form of parabolic QT-RR regression model was used: $QT=\beta \cdot RR^{\alpha}$, where $\alpha$ and $\beta$ were respectively set as $\frac{1}{3}$ and 0.45. In this example, left panel shows one reference recording (i.e., no ventricular arrhythmia) and the right panel shows a ventricular fibrillation (VF) episode recorded from one patient. In both panels, the upper traces plot the recorded RR interval sequence, and the lower traces plot the estimated QT interval sequence (x-axis indexes beats, y-axis unit is ms). The vertical pink bars mark the predicted R-on-T events. Clearly, although ectopic beats occurred frequently in both reference and episode sequences, most of the premature ventricular contractions (PVCs) are "benign", since their RR intervals were longer than the QT intervals estimated from previous cycles. On the other hand, if the PVC occurred early enough as labelled during onset of VF, the R-on-T events are predicted and marked. See FIG. 7: Prediction of R-on-T event at onset of VF but no event for reference recording.

Figure 8:
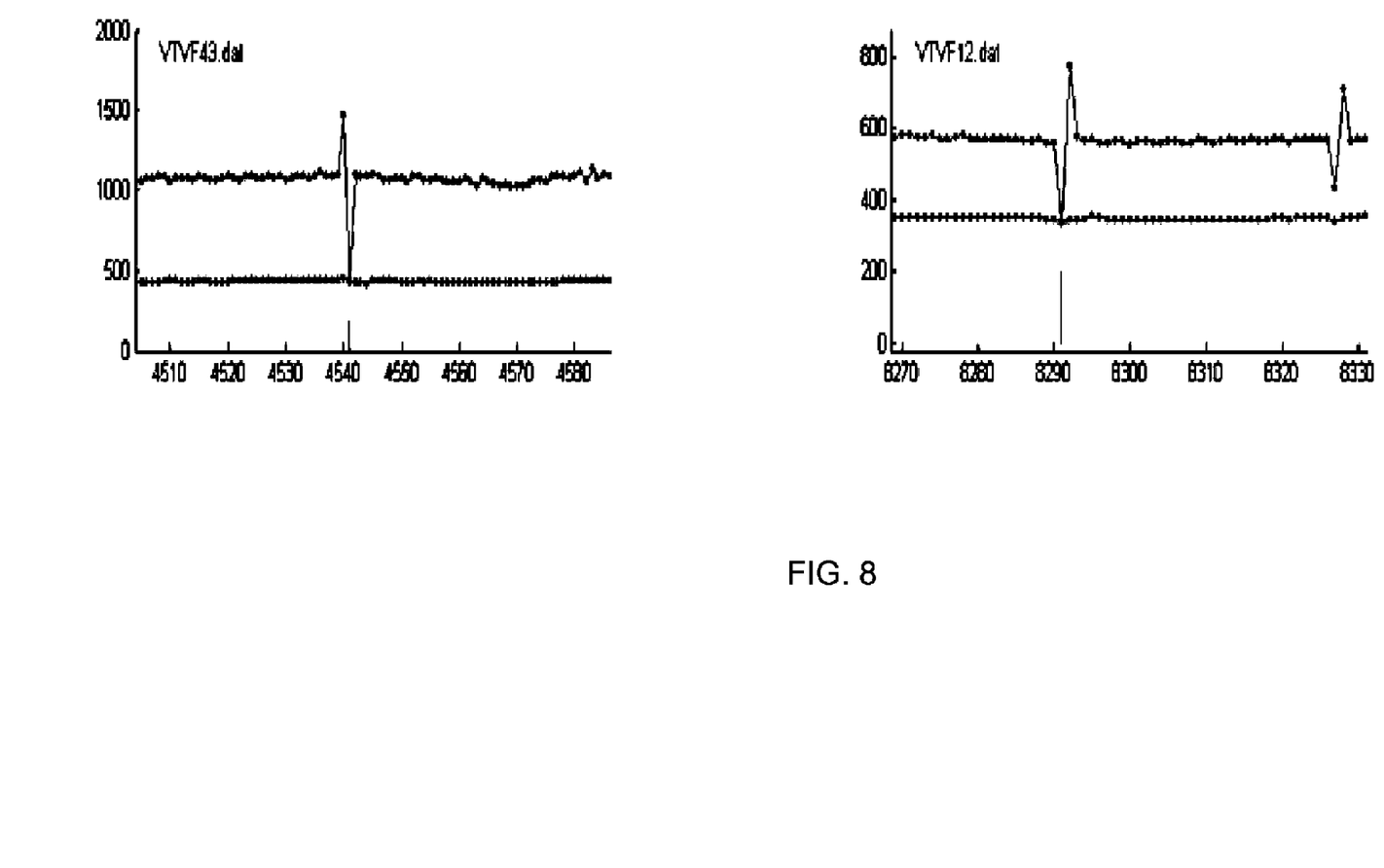
FIG. 8 shows that most predicted R-on-T events can be characterized as long-short-normal or short-long-normal sequence of RR interval, and did not trigger VT/VF.

Similar testing was performed over a database consisting of 85 VT/VF episodes and 52 reference recordings in 38 patients. Very high sensitivity (100%) was achieved, in other words, the R-on-T events were all correctly marked at the onset of VT/VF. On the other hand, the prediction specificity was lower, and more than half reference sequences and many epochs within the VT/VF episodes (but prior to VT/VF onset) were also marked as R-on-T events. This relatively low specificity, however, is expected. Because VT/VF usually is triggered by an R-on-T event, but the R-on-T event does not necessarily trigger VT/VF. The onset of VT/VF relies on critical timing of the PVC to enter the reentry circuit. Even if the PVC sits on the T wave, the probability to trigger VT/VF is still low because such critical timing window may only represent a small portion of the VP. Indeed, most predicted R-on-T events did not trigger VT/VF, and the following RR intervals returned to baseline after the PVC, as the examples shown in FIG. 8. Therefore, in order to further evaluate the risk of VT/VF triggered by the R-on-T event, one simple strategy is to wait for one more beat after the PVC, to see if the next RR interval "recovers" or not. For the same database, such a one-beat delay and re-confirmation strategy can reject more than 95% predicted R-on-T events that did not trigger VT/VF (false positives). See FIG. 8: Most predicted R-on-T events can be characterized as long-short-normal or short-long-normal sequence of RR interval, and did not trigger VT/VF.

Figure 9:
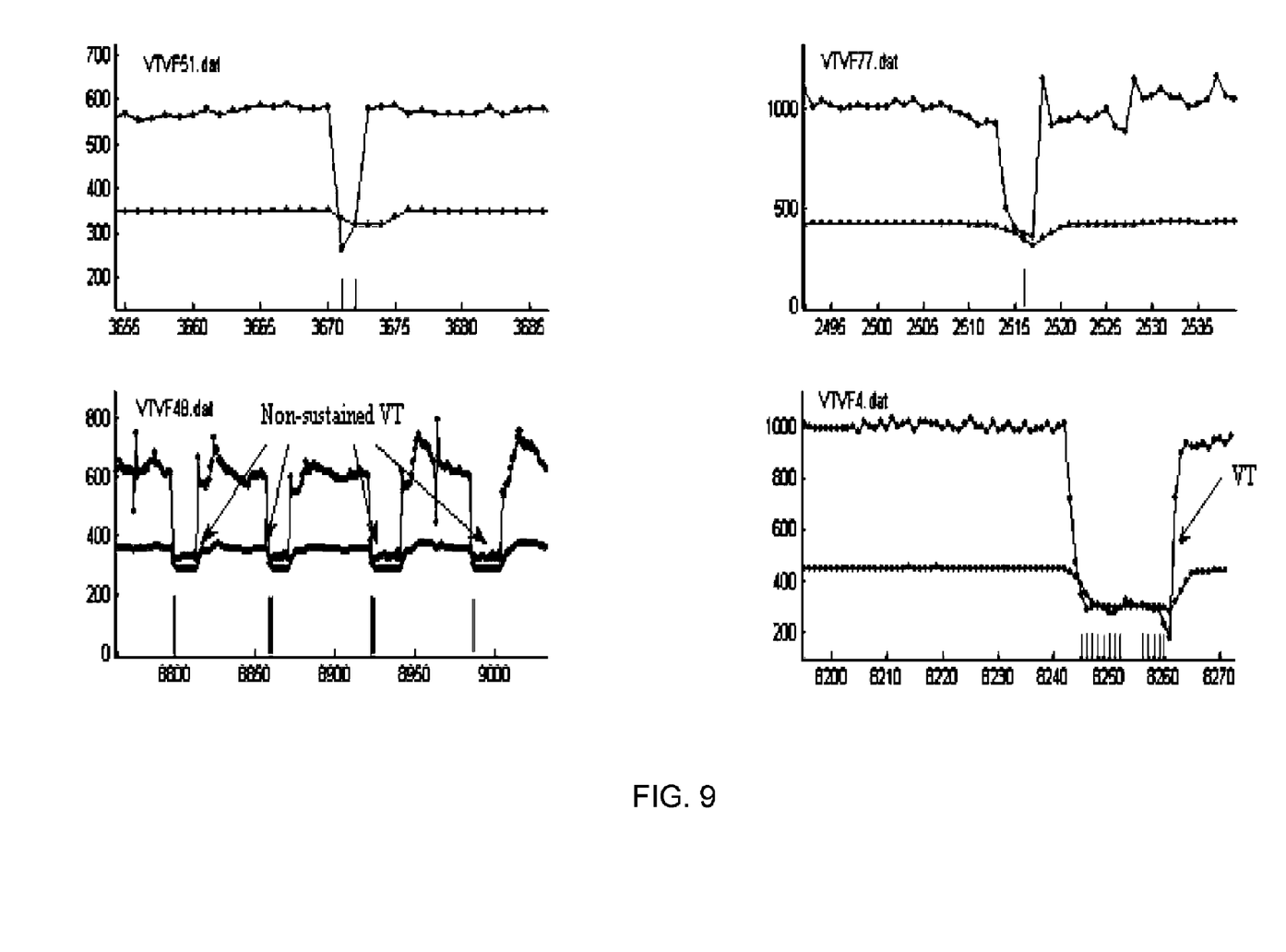
FIG. 9 shows the detection of R-on-T events during epochs of multiple PVCs or at the onset of non-sustained or sustained VT.

For other predicted R-on-T events whose following RR interval did not recover toward the pre-PVC baseline, they can be either characterized as double, triple, multiple PVCs, or can be defined as non-sustained or sustained VT/VF as shown in FIG. 9. Indeed, the multiple PVCs can also be generalized as non-sustained VT with very short duration. Therefore, the present method and its implementation into an implantable or an external device can be used as a marker for VT/VF detection. Of noteworthy is its fast response characteristic, in that it can detect the onset of VT/VF (sustained or non-sustained) within a few beats, as demonstrated in FIG. 9; see FIG. 7: Detection of R-on-T events during epochs of multiple PVCs or at the onset of non-sustained or sustained VT.

Risk Management

As described above, the risk of R-on-T event can be quantitatively assessed using a statistic index RS. According to the present invention, this RS index can be used for VT/VF risk stratification, prediction and prevention.

In a preferred embodiment, the RS index is calculated and stored for each cardiac beat. Thus the distribution of the RS index over certain period is available and its statistics such as mean (RS_MEAN) and standard deviation (RS_STD) can be calculated.

The statistical metrics derived from RS index distribution can be used for risk stratification of ventricular arrhythmia. For example, patient with high RS_MEAN value is considered to have higher risk of developing VT/VF while patient with low RS_MEAN value is considered to have lower risk of developing VT/VF.

In addition, these statistic metrics can be calculated in both short term (for example 5 minutes) and long term (for example 24 hours). Like heart rate variability (HRV) analysis, short term and long term RS metrics may contain different information that are both useful for risk stratification.

The short term RS metrics may also be used for short-term VT/VF prediction. A history of RS values prior to VT/VF onset may be stored and analyzed to characterize the path of the RS dynamics toward the onset of VT/VF. If such RS pattern is detected again, a prediction of VT/VF is made.

Based on VT/VF risk stratification or prediction, therapeutic intervention can be initiated to prevent the onset of VT/VF. Such intervention can be in the form of drug therapy or device therapy, such as overdrive pacing therapies.

Furthermore, the statistic metrics derived from RS index may also be combined with other known risk factor analysis, such as HRV, T wave alternans (TWA), ejection fraction (EF), heart rate turbulence (HRT), etc. Such multi-variable risk analysis may improve the sensitivity and specificity of the VT/VF risk stratification and prediction.

Although an exemplary embodiment of the present invention has been shown and described, it should be apparent to those of ordinary skill that a number of changes and modifications to the invention may be made without departing from the spirit and scope of the invention. In particular, it is possible to implement QT interval analysis and R-on-T risk assessment according to the invention independently from each other either in an implantable medical device or in an external medical device. This invention can readily be adapted to a number of different kinds of medical devices by following the present teachings. All such changes, modifications and alterations should therefore be recognized as falling within the scope of the present invention.

What is claimed is:

1. A medical device comprising:
a memory;
an input configured to receive a cardiac electrogram signal; and,
a processor coupled with said memory and said input wherein said processor is configured to:
detect R-wave and T-waves represented by said cardiac electrogram signal to form one or more binned RR interval range;
establish a QT-RR regression model based on said R-waves and T-waves;
estimate a vulnerable period to provide estimated vulnerable period data based on a distribution of corresponding RT peak to peak intervals or $RT_{PP}$ intervals for each said binned RR interval range, to define boundaries of the vulnerable period for said binned RR interval range;
store said estimated vulnerable period data in said memory.

2. The medical device according to claim 1, wherein said processor is further configured to establish said QT-RR regression model based on said R-waves and T-waves via tests of different regression models including linear model, hyperbolic model, or parabolic model, with different regression parameters to thus determine an optimal QT-RR regression model, which is defined to have a lowest residuum between modeled data and measured data.

3. The medical device according to claim 1, wherein said processor is further configured to conduct said regression analysis offline in an external device, and to program a resulting optimal QT-RR regression model and its parameters into an implantable device.

4. The medical device according to claim 3, wherein said processor is further configured to pre-calculate a QT-RR lookup table based on said QT-RR regression model and to download the QT-RR lookup table into said memory.

5. The medical device according to claim 1, wherein said processor is further configured to estimate said vulnerable period around a peak of a T-wave through determination of the peak of the T wave and set the vulnerable period around the peak of the T wave that is calculated for each heart cycle based on said QT-RR regression model.

6. The medical device according to claim 1, wherein said processor is further configured to define upper and lower boundaries of the vulnerable period for each binned RR interval range as a max/min $RT_{PP}$ interval.

7. The medical device according to claim 1, wherein said processor is further configured to define upper and lower boundaries of the vulnerable period for each binned RR interval so that a programmable percentile of $RT_{PP}$ intervals are distributed between said upper and lower boundaries of the vulnerable period.

8. A medical device comprising:
a memory;
an input configured to receive a cardiac electrogram signal;
a processor coupled with said memory and said input wherein said processor is configured to:
detect R-wave and T-waves represented by said cardiac electrogram signal to form one or more binned RR interval range;
establish a QT-RR regression model based on said R-waves and T-waves;
estimate a vulnerable period to provide estimated vulnerable period data;
store said estimated vulnerable period data in said memory;
calculate a risk score of an R-on-T event RS wherein $$RS = Ae^{-\Delta^2/\sigma^2}$$

with $\Delta$ being an absolute time difference between a next RR interval and a nearest boundary of a current beat's vulnerable period if the next RR interval ends up outside vulnerable period boundaries, and being 0 if the next RR interval ends up within the vulnerable period boundaries, A being a constant, that defines a probability of said R-on-T event in a case of $\Delta=0$, and $\sigma$ that controls a sensitivity of the risk score with respect to a change of $\Delta$, through adjustment of a width of a function curve.

9. A method for determining the vulnerable period and assessing the risk of R-on-T event, comprising the steps:
receiving a cardiac electrogram signal on an input;
detecting R-waves and T-waves represented by said cardiac electrogram signal and forming one or more binned RR interval range;
establishing a QT-RR regression model based on said R-waves and T-waves;
estimating a vulnerable period to provide estimated vulnerable period data based on a distribution of the corresponding RT peak to peak intervals or $RT_{PP}$ intervals for each said binned RR interval range;
defining boundaries of the vulnerable period for said binned RR interval range based on said estimating; and,
storing said estimated vulnerable period data in a memory of a medical device.

10. The method of claim 9, wherein the step of establishing a QT-RR regression model comprises:
testing different regression models including linear model, hyperbolic model, or parabolic model, with different regression parameters; and,
determining an optimal QT-RR regression model, which is defined to have a lowest residuum between modelled data and measured data.

11. The method of claim 9, wherein the step of establishing a QT-RR regression model comprises:
conducting said regression analysis offline in an external device; and,
programming a resulting optimal QT-RR regression model and its parameters into said medical device.

12. The method of claim 11, wherein the step of establishing a QT-RR regression model comprises:
pre-calculating a QT-RR lookup table based on said QT-RR regression model; and, downloading said pre-calculated QT-RR lookup table into said memory.

13. The method of claim 9, wherein the step of estimating the vulnerable period comprises:
    determining a peak of a T wave and then setting the vulnerable period around the peak of the T wave that is calculated for each heart cycle based on said regression model.

14. The method of claim 9, wherein the step of estimating the vulnerable period further comprises:
    defining upper and lower boundaries of the vulnerable period for each binned RR interval range as a max/min $RT_{PP}$ interval.

15. The method of claim 9, wherein the step of estimating the vulnerable period further comprises:
    defining upper and lower boundaries of the vulnerable period for each binned RR interval so that a programmable percentile of the $RT_{PP}$ intervals are distributed between upper and lower boundaries of the vulnerable period.

16. A method for determining the vulnerable period and assessing the risk of R-on-T event, comprising the steps:
    receiving a cardiac electrogram signal on an input;
    detecting R-waves and T-waves represented by said cardiac electrogram signal and forming one or more binned RR interval range;
    establishing a QT-RR regression model based on said R-waves and T-waves;
    estimating a vulnerable period to provide estimated vulnerable period data;
    storing said estimated vulnerable period data in a memory of a medical device;
    calculating a risk score of R-on-T event RS wherein;

$$RS = Ae^{-\Delta^2/\sigma^2}$$

with $\Delta$ being an absolute time difference between a next RR interval and a nearest boundary of a current beat's vulnerable period if the next RR interval ends up outside the vulnerable period boundaries, and being 0 if the next RR interval ends up within the vulnerable period boundaries, A being a constant, that defines a probability of said R-on-T event in a case of $\Delta=0$, and $\sigma$ controlling a sensitivity of the risk score with respect to a change of $\Delta$, by adjusting a width of a function curve.

* * * * *